US009433742B2

(12) United States Patent
Manzke et al.

(10) Patent No.: US 9,433,742 B2
(45) Date of Patent: Sep. 6, 2016

(54) VAPORIZER FILLER AND METHOD OF FILLING A VAPORIZER

(71) Applicants: Russell C. Manzke, Madison, WI (US); Thomas Bender, II, Cottage Grove, WI (US); David G. Barton, Madison, WI (US); Michael S. Morrissey, Madison, WI (US); Robert Q. Tham, Middleton, WI (US)

(72) Inventors: Russell C. Manzke, Madison, WI (US); Thomas Bender, II, Cottage Grove, WI (US); David G. Barton, Madison, WI (US); Michael S. Morrissey, Madison, WI (US); Robert Q. Tham, Middleton, WI (US)

(73) Assignee: General Electric Company, Schenectady, NY (US)

( * ) Notice: Subject to any disclaimer, the term of this patent is extended or adjusted under 35 U.S.C. 154(b) by 0 days.

(21) Appl. No.: 14/688,698

(22) Filed: Apr. 16, 2015

(65) Prior Publication Data

US 2015/0217080 A1 Aug. 6, 2015

Related U.S. Application Data

(63) Continuation of application No. 13/303,719, filed on Nov. 23, 2011, now Pat. No. 9,061,114.

(51) Int. Cl.
*A61M 16/18* (2006.01)
*B65B 3/04* (2006.01)

(52) U.S. Cl.
CPC ............. *A61M 16/183* (2013.01); *B65B 3/04* (2013.01)

(58) Field of Classification Search
CPC .......... A61M 6/10; A61M 6/14; A61M 6/18; A61M 6/183; B65B 3/04
USPC ................ 141/1, 2, 285, 346, 347, 363–366
See application file for complete search history.

(56) References Cited

U.S. PATENT DOCUMENTS

| 5,293,865 A | 3/1994 | Altner et al. |
| 5,381,836 A | 1/1995 | Braatz et al. |
| 5,427,145 A | 6/1995 | Grabenkort |
| 5,470,511 A | 11/1995 | Laybourne et al. |

(Continued)

FOREIGN PATENT DOCUMENTS

| CN | 101426548 A | 5/2009 |
| CN | 101496925 A | 8/2009 |

(Continued)

OTHER PUBLICATIONS

Unofficial English Translation of Chinese Office Action and Search Report issued in connection with corresponding CN Application No. 201210481515.9 on Jul. 1, 2015.

*Primary Examiner* — Timothy L Maust

(57) ABSTRACT

A vaporizer filler includes a fill port. The fill port defines an open interior. The open interior is configured to receive the nozzle of an anesthetic bottle. An agent reservoir is configured to receive and store anesthetic agent. A valve is disposed between the open interior and the agent reservoir. At least one vent extends through the fill port. A method of filling a vaporizer includes inserting the nozzle of a bottle filled with anesthetic agent into a vaporizer filler. At least one vent is occluded from fluid communication. Fluid communication between and open interior and an agent reservoir is opened. Anesthetic agent is poured into an agent reservoir of a vaporizer. Fluid communication is closed between the open interior and the agent reservoir. At least one vent is opened to fluid communication with the open interior. Pressure within the open interior is released through the at least one vent.

9 Claims, 5 Drawing Sheets

(56) References Cited

U.S. PATENT DOCUMENTS

| | | |
|---|---|---|
| 5,505,236 A | 4/1996 | Grabenkort et al. |
| 5,617,906 A | 4/1997 | Braatz et al. |
| 5,676,186 A | 10/1997 | Vanderploeg |
| 5,687,777 A | 11/1997 | Dobson et al. |
| 5,799,711 A | 9/1998 | Heinonen et al. |
| 5,918,595 A | 7/1999 | Olsson et al. |
| 6,125,893 A | 10/2000 | Braatz et al. |
| 6,138,672 A | 10/2000 | Kankkunen |
| 6,585,016 B1 | 7/2003 | Falligant et al. |
| 6,745,800 B1 | 6/2004 | Sansom |
| 6,817,390 B2 | 11/2004 | Falligant et al. |
| 6,929,041 B2 | 8/2005 | Falligant et al. |
| 7,290,571 B2 | 11/2007 | Bunke et al. |
| 7,546,856 B2 | 6/2009 | Chotenovsky |
| 7,886,780 B2 | 2/2011 | Falligant et al. |
| 7,886,783 B2 | 2/2011 | Rindy et al. |
| 8,522,839 B2 | 9/2013 | Freed et al. |
| 9,061,114 B2 * | 6/2015 | Manzke ............... A61M 16/183 |
| 2013/0126464 A1 | 5/2013 | Manzke et al. |

FOREIGN PATENT DOCUMENTS

| | | |
|---|---|---|
| EP | 0723147 A1 | 7/1996 |
| EP | 0909567 B1 | 4/1999 |

* cited by examiner

VAPORIZER FILLER AND METHOD OF FILLING A VAPORIZER

CROSS-REFERENCE TO RELATED APPLICATION

The present application is a continuation of and claims priority to U.S. patent application Ser. No. 13/303,719 filed Nov. 23, 2011, titled "VAPORIZER FILLER AND METHOD OF FILLING A VAPORIZER," the disclosure of which is incorporated herein.

BACKGROUND

The present disclosure is related to the field of anesthesia delivery. More specifically, the present disclosure is related to filling a vaporizer with anesthetic agent. Anesthesia treatment involves delivering one or more drugs to a patient in an attempt to create sedation, analgesia, and neural muscular blockade effect in the patient. Often, these anesthetic drugs are entrained in breathing gases, exemplarily air, to be inhaled by the patient. Handling of anesthetic agents requires particular care due to the physical properties of the agents used, and the medical effects resulting from exposure to anesthetic agents.

Many anesthetic agents are a liquid at room temperature, but exhibit a low boiling point. Three common examples of anesthetic agents include sevoflurane, desflurane, and isoflurane, although others will be recognized by one of ordinary skill in the art. Exemplarily, desflurane has a boiling point of 23.5° C., isoflurane has a boiling point of 48.5° C., and sevoflurane has a boiling point of 58.6° C.

BRIEF DISCLOSURE

In accordance with an embodiment disclosed herein, a vaporizer filler is used in conjunction with a vaporizer and an anesthetic agent bottle having a nozzle. The vaporizer filler includes a fill port defining an open interior. The open interior of the fill port is configured to receive the nozzle of the anesthetic agent bottle. An agent reservoir is configured to receive and store anesthetic agent. A valve is disposed between the open interior and the agent reservoir. The valve is operable to selectively control fluid communication between the open interior and the agent reservoir. At least one vent extends through the fill port. The at least one vent has an inlet on the interior of the fill port at the open interior and the at least one vent has an outlet exterior of the fill port.

In accordance with an alternative embodiment disclosed herein, a vaporizer filler includes a fill port having an open interior. The open interior of the fill port is configured to receive a nozzle of a bottle of anesthetic agent. An agent reservoir is fluidly connected to the open interior to receive and hold liquid anesthetic agent. A valve is disposed between the open interior and the agent reservoir. The valve operates between an open position that permits anesthetic agent to flow from the open interior to the agent reservoir and a closed position that blocks flow of anesthetic agent into the agent reservoir. At least one vent extends away from the open interior.

In accordance with an embodiment disclosed herein, a method of filling a vaporizer includes inserting the nozzle of a bottle filled with anesthetic agent into a vaporizer filler. The vaporizer filler has a fill port with an open interior. The fill port has at least one vent therethrough. The at least one vent is occluded from fluid communication with the open interior. Fluid communication between the open interior and an agent reservoir is opened and anesthetic agent is poured into the agent reservoir. Fluid communication between the open interior and the agent reservoir is closed, and at least one vent is opened to fluid communication with the open interior. Pressure within the open interior is released through the at least one vent.

BRIEF DESCRIPTION OF THE DRAWINGS

The drawings illustrate the best mode presently contemplated of carrying out the disclosure. In the drawings.

DETAILED DESCRIPTION

Figure 1:
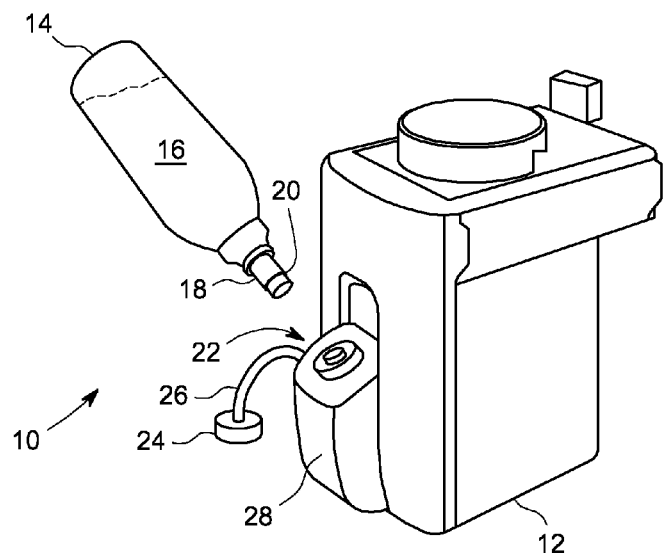
FIG. 1 is an isometric view in accordance with an embodiment of the vaporizer filler system disclosed herein.

FIG. 1 is an isometric view of a vaporizer filler system 10. The vaporizer filler system 10 includes a vaporizer filler 12. In one embodiment, the vaporizer filler 12 may be an integral part of a vaporizer, in another embodiment, the vaporizer filler may be a cassette that is inserted into a vaporizer. The vaporizer filler system 10 further includes a bottle 14 that holds liquid anesthetic agent 16. The bottle 14 terminates at one end in a nozzle 18. The nozzle 18 is configured to pour the anesthetic agent 16 out of the bottle 14. Embodiments of the nozzle 18 can be designed to selectively pour the anesthetic agent 16 out of the bottle 14. Such designs for a selectively operable nozzle are known to those of ordinary skill in the art, and include, but are not limited to friction fit, push valves and caps. Embodiments of the nozzle 18 further include a seal 20 which is exemplarily depicted as an elastomeric O-ring. However, it is understood that alternative types of seals and/or gaskets as would be recognized by one of ordinary skill in the art, may be used in embodiments incorporating this seal 20.

The vaporizer filler 12 contains an agent reservoir (not depicted) that is configured to receive and store the anesthetic agent poured into the vaporizer filler 12 from the bottle 14. The vaporizer filler 12 includes a fill port 22 that is configured to receive the nozzle 18 of the bottle 14. A cap 24 is secured to the vaporizer filler 12 with a tether 26. The cap 24 is configured to secure over the fill port 22 exemplarily by screw fit or friction fit.

Figure 2A:
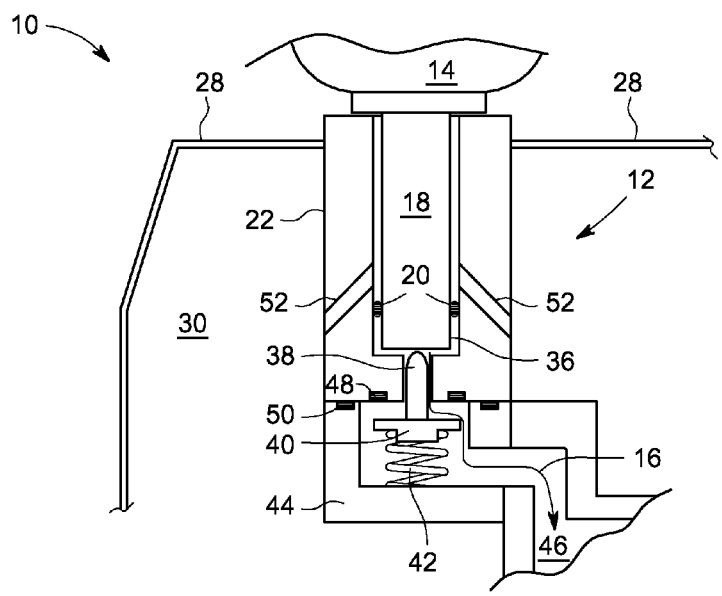
FIG. 2A is a cutaway view of an embodiment of the vaporizer filler system with a valve in an open position.
Figure 2B:
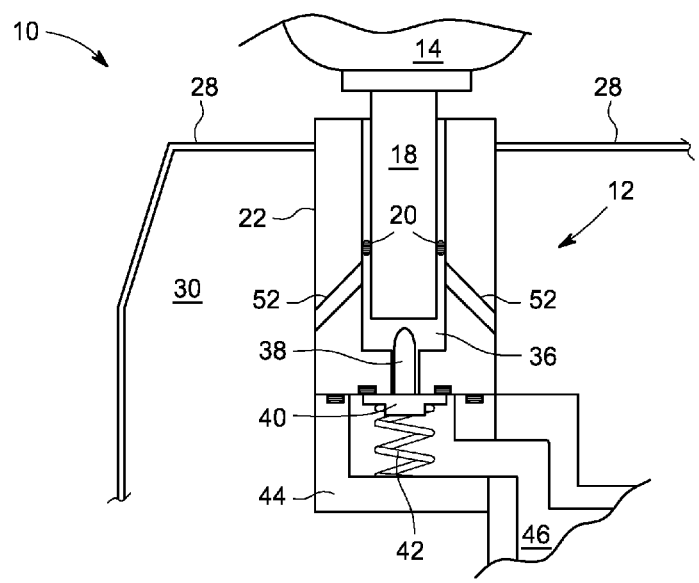
FIG. 2B is a cutaway view of an embodiment of the vaporizer filler system with a valve in a closed position.

FIGS. 2A and 2B depict cross sectional views of the vaporizer filler system 10, including the bottle 14 and the vaporizer filler 12. FIGS. 2A and 2B depict the nozzle 18 of the bottle 14 at two different positions within the fill port 22 in the embodiment depicted in FIG. 2B the nozzle 18 is only partially inserted within the fill port 22, while FIG. 2A depicts the nozzle 18 fully inserted within the fill port 22.

The fill port 22 defines an open interior 36 that is configured to receive at least a portion of the nozzle 18 of the bottle 14.

Referring to FIG. 2A, when the nozzle 18 is fully inserted into the open interior 36 of the fill port 22, the nozzle 18 engages an actuator 38 of a valve 40. The valve 40 is biased in a closed position, such as by a spring 42. It is to be understood that in alternative embodiments, the valve 40 can be biased in the closed position in a variety of manners including, but not limited to, other configurations of deformable or resilient components. Similarly, based upon the construction of the valve, alternative forms of actuators may be used within the scope of the disclosure.

The valve 40 controls the fluid communication between the open interior 36 of the fill port 22 and a filler manifold 44 which is fluidly connected to an agent reservoir 46. The agent reservoir 46 is configured to hold and retain the anesthetic agent 16 that flows out of the nozzle 18, through the valve 40 in the open position, and into the filler manifold 40 and the agent reservoir 46. Seals 48 and 50, which may exemplarily be elastomeric O-rings, provide seals against fluid communication, respectively, between the valve 40 in the closed position and the fill port 22, and the fill port 22 with the filler manifold 44.

Thus, FIG. 2A depicts the vaporizer filler system 10 when the agent reservoir 46 is being actively filled with anesthetic agent 16 flowing out of the nozzle 18 of the bottle 14. After the agent reservoir 46 has been filled, or alternatively, when the bottle 14 has been emptied of anesthetic agent 16, the bottle 14 and nozzle 18 are retracted from the vaporizer filler 12.

It has been observed by the inventors that under certain conditions, exemplarily elevated temperatures of the anesthetic agent in the bottle or agent reservoir and/or an overfilled agent reservoir, the open interior 36 of the fill port 22 can become pressurized between the seal 20 and the valve 40 in the closed position. As previously noted, anesthetic agents may exhibit a relatively low boiling point and therefore a relatively small elevation in temperature can transition the anesthetic agent from liquid to a gas state, increasing the pressure within the small space of the open interior 36. It has further been observed that when nozzle 18 is fully removed from the fill port 22, and in particular, the seal 20 is removed from the fill port 22, the pressurized gas within the open interior 36 can be rapidly ejected from the fill port 22, including the anesthetic agent liquid or vapor.

In order to alleviate this build-up of pressure, the fill port 22 includes at least one vent 52 that extends from the open interior 36 through the fill port 22. In some embodiments disclosed herein, a single vent 52 extends from the open interior 36. In other embodiments, multiple vents are circumferentially spaced about the bore 30. In one non-limiting example, nine vents 52 are spaced about the fill port 22. In a still further non-limiting example, multiple vents 52 are directed in a single direction such as to further minimize any impact from the exhaust through the vents 52.

FIG. 2B depicts a partially withdrawn bottle 14 and nozzle 18 from the vaporizer filler 12. To arrive at the position of the bottle 14 depicted in FIG. 2B, the nozzle 18 is first withdrawn to the extent that the nozzle disengages the actuator 38, closing the valve 40. At the point at which the valve 40 closes, the seal 20 engages the fill port 22 at a position below the vents 52. The vents 52 are positioned such that the seal 20 engages the fill port 22 at a position below the vents 52 when the valve 40 is in the open position, as depicted in FIG. 2A, as well as when the valve 40 is in the closed position. As the nozzle 18 is withdrawn further from the fill port 22, the seal 20 moves above the vents 52, arriving at the position depicted in FIG. 2B. When the seal 20 is above the vents 52 and the valve 40 is closed, any excessively pressurized gas and anesthetic agent within the open interior 36 is released through the vents 52. In FIG. 2B, the vent 52 connects the open interior 36 to the ambient air, and the pressure within the open interior 36 is equalized with the ambient atmosphere pressure. As further shown in FIG. 2B, the at least one vent 52 is angled through the fill port 22 in a direction away from the bottle 14, and presumably any user manually withdrawing the bottle 14 and nozzle 18 from the fill port 22.

In the embodiment of the vaporizer filler 12 depicted in FIGS. 2A and 2B, the vaporizer filler further includes a cover 28 that extends about at least a portion of the fill port 22. The cover 28 may provide aesthetic, or finish aspects to the vaporizer filler 12. Additionally, embodiments of the cover 28 may provide protection to the structures of the vaporizer filler 12 contained within. In embodiments that include a cover 28, the at least one vent 52 may be arranged through the fill port 22 in order to vent the pressurized gas and anesthetic agent into a space 30 defined between the cover 28 and the fill port 22. In one non-limiting embodiment, the space 30 includes a connection to a gas scavenger (not depicted) such that any anesthetic agent entrained in the vented pressurized gas can be captured.

While details of the operation of the bottle 14 and nozzle 18 are not included herein, it will be recognized that embodiments of the bottle 14 and nozzle 18 may include various mechanisms in order to operate the nozzle 18 between opened and closed configurations that permit or restrict the flow of anesthetic agent out of the bottle 14. In non-limiting examples, the insertion of the nozzle 18 into the fill port 22 can actuate the nozzle 18 such as to move the nozzle into an open configuration. Alternatively, the actuator 38 may additionally actuate the nozzle 18 to move from a closed position into an open position, wherein when the nozzle 18 disengages from the actuator 38, the nozzle 18 also moves into a closed position. As these are non-limiting examples, a person of ordinary skill in the art will recognize a variety of alternative solutions by which the flow of anesthetic agent out of the bottle 14 can be controlled. It is also to be noted that in embodiments, the nozzle 18 is closed to fluid communication while the nozzle 18 is in a position such that the seal 20 is below the vents 52. After the nozzle 18 is closed to fluid communication, the nozzle is withdrawn to place the seal 20 in a position above the vents 52 in accordance with such embodiments.

Figure 3:
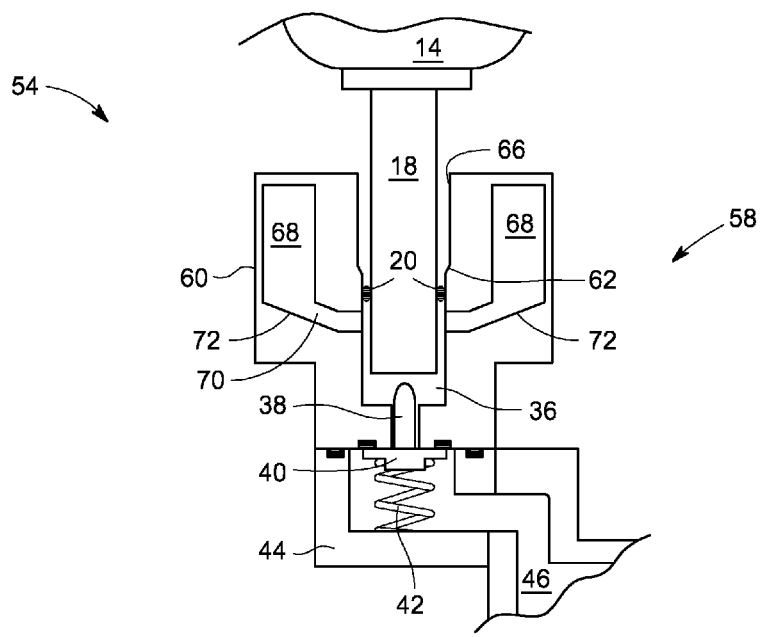
FIG. 3 is a cutaway view of an alternative embodiment of a vaporizer filler system.

FIG. 3 depicts an alternative embodiment of a vaporizer filler system 54. It is to be recognized that in the embodiment of the vaporizer filler system 54, like reference numerals have been used to indicate like components as depicted and described above with respect to the previous figures. It is also to be noted that the features of various embodiments may be combined or rearranged by one of ordinary skill in the art beyond the specific embodiments disclosed to arrive at alternative embodiments, within the scope of the present disclosure.

The bottle 14 includes a nozzle 18. It is to be understood that various constructions of the nozzle 18 may be used in conjunction with embodiments of the vaporizer filler system 54. The nozzle 18 includes a seal 20.

The vaporizer filler 58 depicted in FIG. 3 includes an alternative construction of the fill port 60. The fill port 60 also has an open interior 66 that is dimensioned to be larger in circumference, than the open interior 36 found lower in the fill port 60. The open interior 66 is dimensioned such that the seal 20 loosely fits within the diameter of the open interior 66 with little deformation, while the open interior 36 is dimensioned to be smaller, thus requiring more deformation of the seal 20 to tightly retain the nozzle 18 within the fill port 60. Thus, the seal 20 creates a loose seal with the open interior 66 and a tight seal with the open interior 36.

Embodiments having an open interior 66 of a first diameter and an open interior 36 of a second, smaller diameter can be implemented in a variety of ways, including a stepped embodiment as pictured in FIG. 3, or a tapered embodiment (not depicted). In the stepped embodiment, the transition between the first diameter of the open interior 66 and the second diameter of the open interior 36 is made over a short distance across a step 62 on the interior of the fill port 60 between the open interior 66 and the open interior 36. In the tapered embodiment, a gradual transition is made along the fill port 60 between the first diameter of the open interior 66 and the second diameter of the open interior 36.

The embodiment of the fill port 60 depicted in FIG. 3 has been discovered by the applicants to provide reduced wear, greater product longevity and reliability. The larger circumferenced open interior 66 of the fill port 60 provides less wear and deformation of the seal 20, while still providing an adequate fluid seal such as to divert the excess pressure from the open interior 36 through the at least one vent 70. The smaller circumferenced open interior 36 still maintains the tight seal between the nozzle 18 and the fill port 60 for transfer of the liquid anesthetic agent into the agent reservoir. This is not intended to be limiting on the nozzle connection methods used in conjunction with embodiments of the fill port 60 with stepped or tapered interiors.

The vaporizer filler 58 is further constructed to include one or more expansion chambers 68. The expansion chambers 68 are connected to the open interior 36 through at least one vent 70. The expansion chamber 68 is dimensioned such that when excess pressure, including anesthetic agent liquid or vapor is released from the open interior 36 through the vents 70, the additional volume of the expansion chamber is sufficient to reduce the pressure within the open interior 36 in such a manner as to reduce or eliminate any rapid ejection of the remaining pressurized gas and anesthetic agent through the fill port 60 upon removal of the nozzle 18 from the bottle 14. The additional volume of the expansion chamber 68 reduces the overall pressure in the combined volume of the open interior 36 and the expansion chamber 68. Thus, the elevated pressure from the open interior 36 is equalized across the additional volume and, according to the laws of fluid dynamics, pressure across the combined volume of the open interior 36 and the expansion chamber 68 is reduced, mitigating any spray or exhaust when the seal 20 is fully withdrawn from the open interior 66.

It is to be recognized that the expansion chamber 68, as depicted in FIG. 3, is but one exemplary embodiment of the construction of such an expansion chamber 68. Alternative embodiments of the expansion chamber 68 may be positioned downward from the vent 70, exemplarily in the direction of the agent reservoir 46. Additionally, the expansion chamber 68 is depicted as being constructed integral to the fill port 60. It is to be recognized that in alternative embodiments, the expansion chamber 68 is a component separate from the fill port 60 and may be circumferentially disposed about the fill port 60, or aligned with vents 70 to one side of the fill port 60. In another embodiment, the expansion chamber can be a separate component that is connected to a single vent through the fill port 60 by a tube (not depicted) such that the expansion chamber can be located remotely from the fill port 60. In a still further embodiment, the expansion chamber can be opened to the ambient air at a portion of the expansion chamber that is remote from the vent connecting to the open interior of the bore. The increased volume provided by the expansion chamber mitigates any spray of anesthetic agent liquid or vapor, while the open connection to the ambient air further mitigates any release of pressure from the open interior.

Some embodiments of the expansion chamber 68 include an angled portion 72 as an additional feature. Anesthetic agent liquid or vapor enters the expansion chamber after the vent 70 is opened to fluid communication with the open interior 36. The expansion chamber can collect any anesthetic agent liquid and permit anesthetic agent vapor to condense back into anesthetic liquid. The liquid anesthetic agent is then directed by the angled portion 72 back into the open interior 36 for collection. Any remaining anesthetic liquid can be delivered to the agent reservoir 46 upon the next actuation of the valve 40 for filling the agent reservoir 46.

It is to be understood that in alternative embodiments, the expansion chamber 68 may be configured such as to direct collected anesthetic agent liquid or vapor away from the vent 70 and the open interior 36 where it can be either collected for disposal, or vented to the exterior of the fill port 60.

Figure 4:
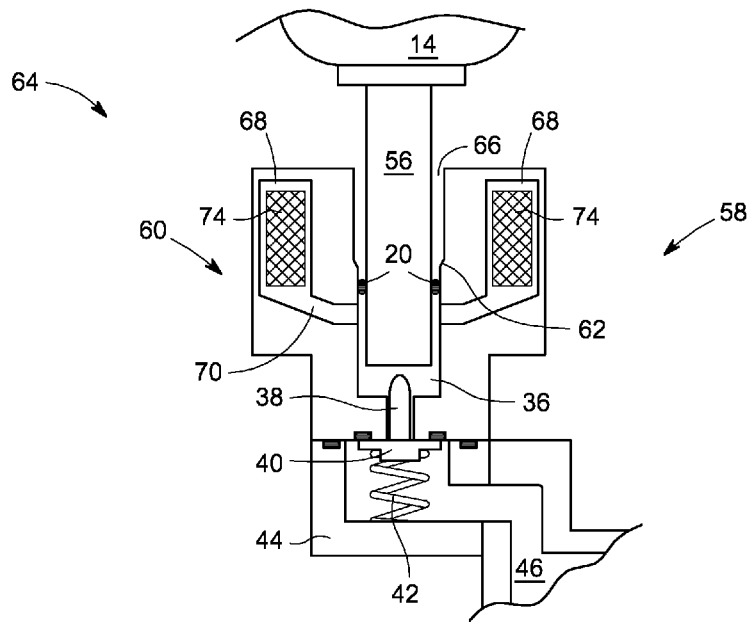
FIG. 4 depicts an aspect of an embodiment alternative to the embodiment of the vaporizer filler system depicted in FIG. 3.

FIG. 4 depicts an alternative embodiment of a vaporizer filling system 64. The vaporizer filler 58 includes a fill port 60 with a step 62 between the open interior 66 and the open interior 36. Vaporizer filler 58 is an exemplary embodiment of a vaporizer filler that may use a friction fit to secure the nozzle 56 to the fill port 60. In addition to providing a non-limiting embodiment of a friction fit connection, the embodiment of the vaporizer filler 58 depicted in FIG. 4 further includes a retainer 74 disposed within the expansion chamber 68. The retainer 74 serves the purpose of providing additional surface area to accumulate, collect, and retain anesthetic agent liquid or vapor that is vented into the expansion chamber 68. The retainer 74 can be constructed in a variety of ways. Exemplarily, the retainer 74 can be constructed of stainless steel or ceramic and may take the form of a pad of non-woven fibers, a mesh grid, one or more perforated plates or a porous block. Alternatively, the retainer 74 may be constructed of synthetic or polymeric material, exemplarily a foam or non-woven fiber pad which can be exemplarily constructed of a hydrophilic material. These are intended to be non-limiting examples of the retainer 74.

While not depicted, alternative embodiments of the vaporizer filler that incorporate a retainer may be used within the scope of the present disclosure. Such a retainer may be alternatively located within the open interior 36. In still further embodiments, a retainer (not depicted) may be used in conjunction with the vaporizer filler 12 as depicted in FIGS. 2A and 2B. In such an embodiment, the retainer may be positioned within the open area 30 and in alignment with one or more vents 52 such as to collect any of the anesthetic agent liquid or vapor expelled through the one or more vents 52 for controlled evaporation of the expelled anesthetic agent.

Figure 5:
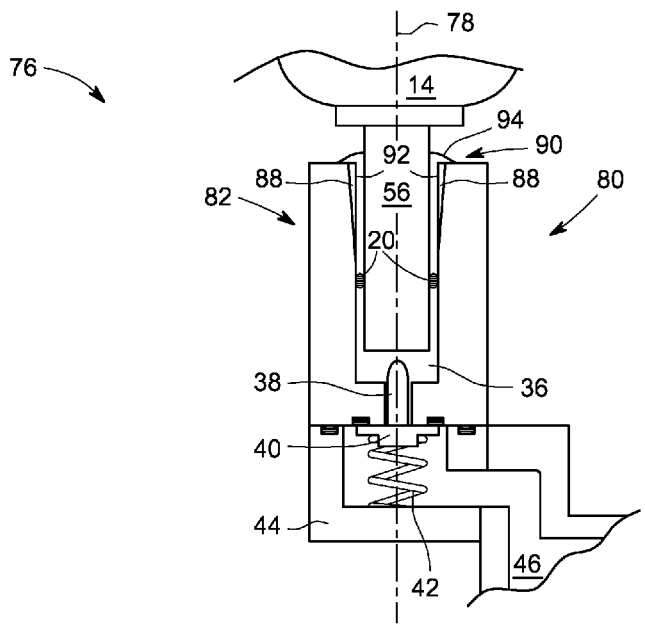
FIG. 5 is an alternative embodiment of a vaporizer filler system.

FIG. 5 depicts another embodiment of a vaporizer filler system 76. The vaporizer filler system 76 includes a vaporizer filler 80 having a fill port 82. The fill port 82 defines an open interior 36 which is susceptible to pressure build up upon the closure of the valve 40. The open interior 36 is aligned within the fill port 82 along a major axis 78 of the open interior 36 and fill port 82. The nozzle 56 fits within the fill port 82 along this major axis 78.

At least one vent 88 extends upwardly through the fill port 82 to the top 90 of the fill port 82. Thus, vent 88 in the embodiment depicted in FIG. 5 extends upwards with respect to the major axis 78. Comparing the embodiment depicted in FIG. 5 to the embodiments depicted in FIGS. 2-4, and described above, the at least one vent in each of these embodiments exemplarily depict alternative orientations between the vent and the major axis of the fill port. Thus, in embodiments disclosed herein, a vent may be directed upwards from, downwards from, or perpendicular to the major axis of the fill port. Further, it is to be recognized that in embodiments of the vaporizer filler, the fill port and the major axis may also be angled, such as is nominally depicted in FIG. 1 to facilitate insertion and removal of the bottle nozzle therefrom. In such embodiments, the angle of the vent may still be oriented in relationship to the major axis, which may thus be apart from vertical.

In one embodiment, the at least one vent 88 is a groove that is cut into the fill port 82 that creates a progressively larger opening for the venting of the excess pressurized gas and anesthetic agent from the open interior 36 as the seal 20 is retracted up and out of the fill port 82. The fill port 82 includes an interior wall 92 that generally maintains the engagement of the seal 20 with the interior of the fill port 82. The at least one vent 88 is therefore designed as a channel progressively extending into the fill port 82 such that a greater opening between the open interior 36 and the exterior of the fill port 82 is created as the nozzle 56 is retracted from the fill port 82.

As depicted in FIG. 5, embodiments of the at least one vent can be shaped to progressively increase or decrease in cross section as the at least one vent progresses through the fill port. Progressively increasing the cross section area can reduce the speed of the exhausted anesthetic agent liquid or vapor to conserve stagnation enthalpy as static pressure increases across the at least one vent. Progressively decreasing the cross sectional area can reduce the flow rate of exhausted anesthetic agent liquid or vapor by increasing the pressure drop across the at least one vent. While the use of at least one vent of progressively increasing or decreasing cross section is herein described with respect to FIG. 5, it is to be understood that this technique may be used in any of the embodiments described herein.

In an embodiment of the vaporizer filler 80, the top 90 of the fill port 82 further includes at least one spray shield 94. The spray shield 94 blocks any anesthetic agent that is expelled through the at least one vent 88 during the retraction of the nozzle 56. The anesthetic agent blocked by the spray shield 94 can either evaporate or be returned to the open interior 36 through the at least one vent 88. In embodiments, the spray shield 94 can be constructed of a flexible material such as to loosely engage the nozzle 56, while being deformable to easily allow the insertion and withdrawal of the nozzle 56 and seal 20 into and out of the fill port 82.

Figure 6:
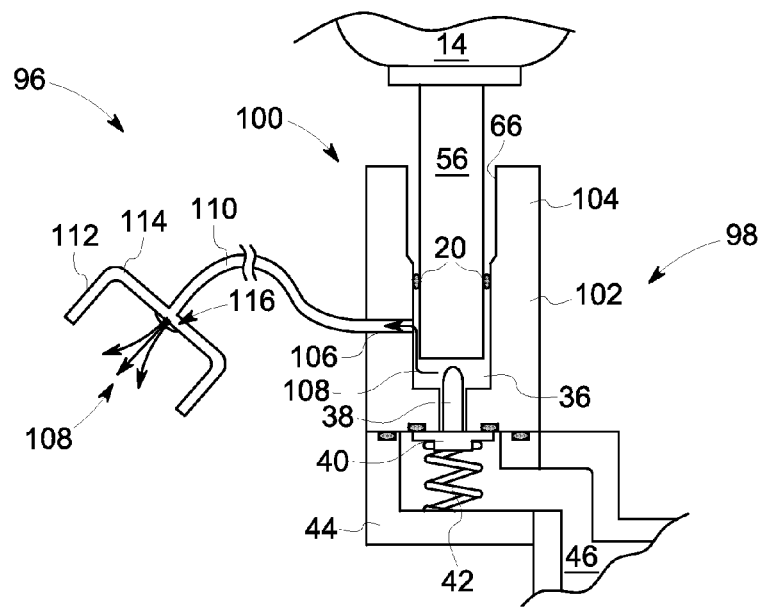
FIG. 6 is a still further alternative embodiment of a vaporizer filler system.

FIG. 6 depicts a still further embodiment of a vaporizer filler system 96. In this alternative embodiment, the vaporizer filler 98 includes a fill port 100. Fill port 100 includes a vent 106, which may, in alternative embodiments, include multiple vents. When the nozzle 56 is withdrawn from the fill port 100 such that the seal 20 is moved above the vent 106, the open interior 36 is opened to fluid communication with the vent 106.

The vaporizer filler system 96 is similar in construction to that depicted in FIG. 1, in that a fill port cap 112 is connected to the vaporizer filler 98 by a tether 110. However, in the vaporizer filler system 96, the tether 110 is hollow and is directly connected to the vent 106. Anesthetic agent liquid or vapor that is pressurized within the open interior 36 is directed through the vent 106 and into the hollow tether 110 where the anesthetic agent 108 is directed into a hollow interior 114 of the fill port cap 112 and out through an exhaust port 116 in the fill port cap 112.

In this embodiment, the expelled anesthetic agent is directed away from the anesthetic agent bottle 14 and any user removing such a bottle. When the fill port 100 is not in use, the fill port cap 112 can be secured over the fill port 100 to protect the fill port 100 and prevent any release of anesthetic agent from the vaporizer filler 98.

Figure 7:
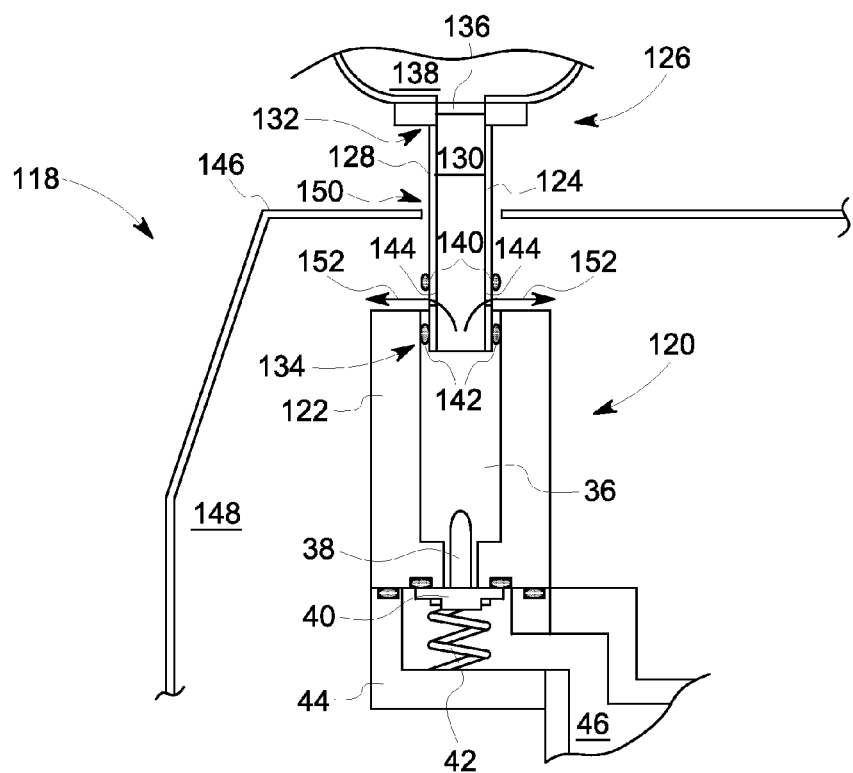
FIG. 7 is an alternative embodiment of a vaporizer system with a bottle in accordance with an alternative embodiment.

FIG. 7 depicts a still further embodiment of a vaporizer filler system 118. The vaporizer filler system 118 includes a vaporizer filler 120 with a fill port 122 that is configured to receive a nozzle 124 of a bottle 126 that is filled with liquid anesthetic agent.

The nozzle 124 and bottle 126 are depicted in cross section in FIG. 7 in order to provide additional detail of the bottle 126 and nozzle 124 of this embodiment. An outer wall 128 of the nozzle 124 defines a channel 130 that runs interior of the outer wall 128 from a bottle end 132 of the nozzle 124 to a vaporizer end 134 of the nozzle 124. A valve 136 is disposed at the bottle end 132 between the nozzle 124 and a liquid agent reservoir 138 of the bottle 126. The valve 136 may be any of a variety of valves as disclosed herein, or as recognized by one of ordinary skill in the art, including, but not limited to, check valves, selectively operable valves, and manually operated valves.

In the embodiment of the bottle 126 depicted in FIG. 7, a first annular seal 140 and a second annular seal 142 are disposed about an exterior of the outer wall 128 at the vaporizer end 134 of the nozzle 124. While in this non-limiting embodiment the first annular seal 140 and the second annular seal 142 are located at the vaporizer end 134, it is to be understood that the seals may be respectively located at various other positions on the nozzle 124. A vent 144 extends through the outer wall 128. The vent 144 is located along the nozzle 124 between the first annular seal 140 and the second annular seal 142. In the embodiment of the bottle 126 depicted in FIG. 7, two vents 144 are depicted; however, it should be recognized that any number of vents may be used in embodiments within the scope of the disclosure. It is to be recognized that in some embodiments of the bottle 126, the vent 144 is disposed through the outer wall 128 in a predetermined direction, or orientation, as will be described in further detail herein.

In use, the vaporizer filler system 118 operates in a similar manner as described above with respect to other embodiments in this disclosure. The nozzle 124 is inserted through an opening 150 in a cover 146 of the vaporizer filler system 118. The cover 146 defines a space 148, as will be described in further detail herein. The vaporizer end 134 of the nozzle 124 passes through the opening 150 and into the fill port 122. When the nozzle 124 is fully inserted within the fill port 122, the valve 40 and valve 136 are opened in order to permit anesthetic liquid or vapor to be delivered from the bottle 126 into the anesthetic agent reservoir 46.

After the reservoir 46 has been filed with liquid anesthetic agent, as disclosed above, the nozzle 124 is withdrawn from the fill port 122 and the possibility exists for pressurized gas and anesthetic agent to build up within the open interior 136 of the fill port 122. Therefore, the user that is withdrawing the nozzle 124 from the fill port 122 partially withdraws the nozzle 124 to a position wherein the first annular seal 140 is moved out of contact with the fill port 122 while the second annular seal 142 maintains contact with the fill port 122. By this arrangement, depicted in FIG. 7, the pressurized gas and anesthetic agent vapor 152 is released out of the open interior 36 through the vent 144 into the space 148. By maintaining a fluid seal at the second annular seal 142, the predetermined direction and venting control provided by the vent 144 may manage and direct the released gas and anesthetic agent vapor in a manageable manner. As described above, in some embodiments, the vent 144 through the outer wall 128 is directed in a predetermined direction in order to direct the released gas and anesthetic agent in a predetermined direction. Non-limiting directions, include released gas that is angled upwards, angled downwards, or angled horizontally into the space 148.

While not depicted, alternative embodiments may include an interruption feature, exemplarily a stop or catch on the fill port. The interruption feature would interact with a portion of the nozzle to slow or restrain the withdrawal of the nozzle from the fill port when the nozzle is in a position where fluid communication through the vent releases the pressurized anesthetic agent liquid or vapor, but before the nozzle has been fully withdrawn from the fill port. In still further embodiments, a visible indication can remind or prompt the user to pause in the withdrawal of the nozzle from the fill port to permit the anesthetic agent liquid or vapor to be released through the vent, prior to fully withdrawing the nozzle.

Figure 8:
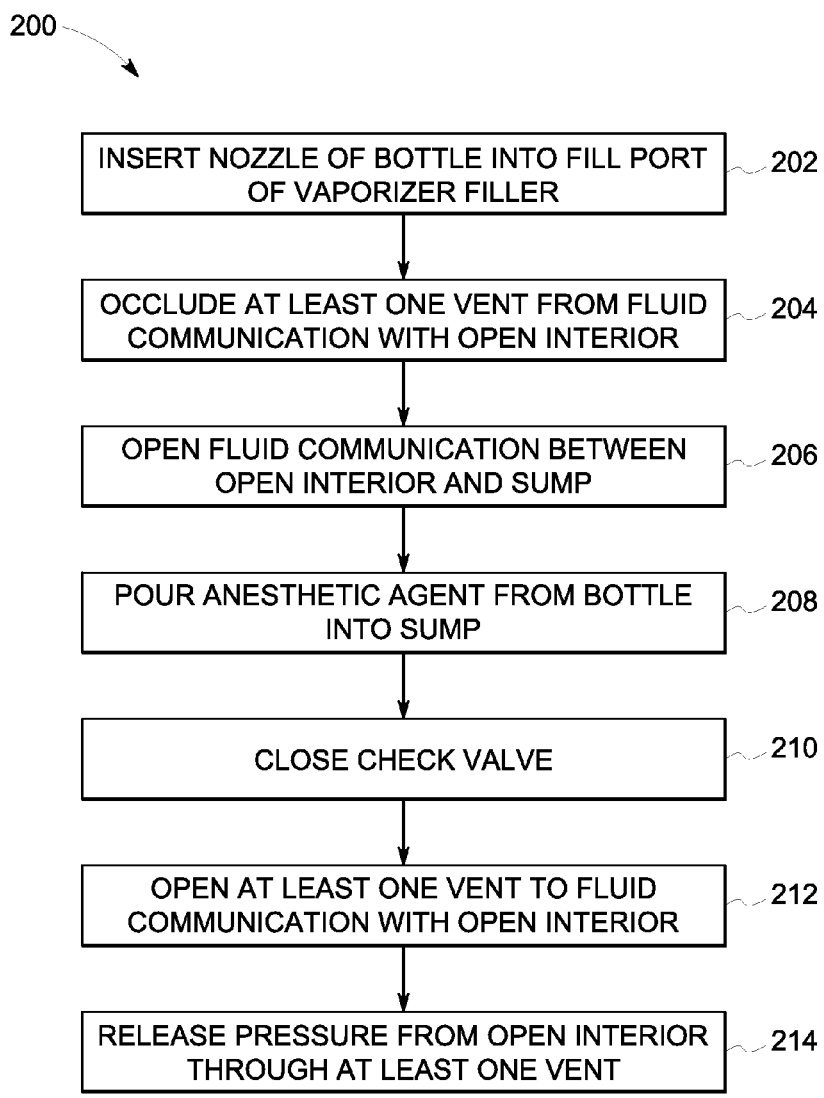
FIG. 8 is a flow chart that depicts an embodiment of a method of filling a vaporizer disclosed herein.

FIG. 8 is a flow chart that depicts an embodiment of a method 200 of filling a vaporizer. The method 200 starts at 202 with the insertion of a nozzle of a bottle filled with anesthetic agent into a fill port of a vaporizer filler. As described above, it is understood that a variety of configurations for the nozzle and the fill port may be used within the presently disclosed method, including, but not limited to, a friction fit between the nozzle and the fill port. In some embodiments of the method, the nozzle of the bottle includes a seal, exemplarily an elastomeric seal that at least partially deforms when in contact with at least a portion of the fill port.

At 204, a vent through the fill port it is occluded from fluid communication with an open interior of the fill port. As described as above, in some embodiments, the open interior is defined between a bore of the fill port and the seal of the nozzle at least partially inserted into the fill port.

In one embodiment, the at least one vent is occluded by translating the seal that is arranged about the nozzle of the bottle within the open interior such that the seal moves past the at least one vent which thereby occludes fluid communication between the open interior and the at least one vent.

Fluid communication between the open interior and an agent reservoir of the vaporizer is opened at 206. As described above, in some embodiments, such fluid communication can be opened by actuating a valve that is disposed between the open interior and the agent reservoir. In one non-limiting example, the valve can be actuated through the insertion of the nozzle into the open interior of the bore where the nozzle presses on an actuator of the valve, moving the valve into an open position. It is to be understood by a person of ordinary skill in the art that alternative manners of opening fluid communication between the open interior and the agent reservoir may be used and are contemplated within the presently disclosed method, such alternative manners can include, but are not limited to other interactions with the nozzle or a user actuated valve.

At 208 anesthetic agent is poured from the bottle into the agent reservoir. The anesthetic agent leaves the nozzle of the bottle, flows through the open interior, and into the agent reservoir of the vaporizer.

In some embodiments, between the occlusion of the at least one vent from fluid communication with the open interior at 204 and pouring the anesthetic agent from the bottle into the agent reservoir 208, additionally, the nozzle of the bottle is opened to fluid communication. This may be performed in a variety of ways, including using various interactions between the nozzle and the fill port.

In such embodiments wherein the nozzle includes a bottle valve that controls the fluid communication between the bottle out of the nozzle, after the agent reservoir has been filled, the bottle is further manipulated such as to close the bottle valve located within the nozzle. Filling of the agent reservoir with anesthetic agent can either be terminated when all of the anesthetic agent from the bottle has flowed into the agent reservoir, or in the event that the agent reservoir is full, a bottle valve within the nozzle can be closed such as to end additional flow of anesthetic agent into the agent reservoir.

After the filling of the agent reservoir with the anesthetic agent from the bottle is completed at 208, the fluid communication between the agent reservoir and the open interior is closed at 210 by closing the valve between the open interior and the agent reservoir. As noted above, in the event that the agent reservoir is too full or if the anesthetic agent is heated to a temperature that approaches or exceeds its boiling point, the anesthetic agent liquid or vapor trapped in the open interior between the seal of the nozzle and the valve closing the fluid communication between the open interior and the agent reservoir can create a condition of elevated pressure within the open interior.

At 212 at least one vent is opened to fluid communication with the open interior. In one embodiment, the at least one vent is opened by withdrawing the nozzle of the bottle at least partially from the fill port such that a seal of the nozzle is located above the at least one vent.

At 214 the pressurized anesthetic agent liquid or vapor is released from the open interior through the at least one vent. The at least one vent can connect to the ambient air outside of the fill port, can be directed into an expansion chamber, or may be directed away from the fill port in a variety of other configurations such as, but not limited to those specifically disclosed in the present disclosure.

This written description uses examples to disclose the invention, including the best mode, and also to enable any person skilled in the art to make and use the invention. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal languages of the claims.

What is claimed is:
1. A method of filling a vaporizer, the method comprising:
 inserting a nozzle of a bottle filled with anesthetic agent into a vaporizer filler, the vaporizer filler having a fill port with an open interior;
 occluding at least one vent in the fill port from fluid communication with the open interior;
 opening fluid communication between the open interior and an agent reservoir;
 pouring the anesthetic agent into the agent reservoir;

closing fluid communication between the open interior and the agent reservoir;

opening the at least one vent in the fill port to fluid communication with the open interior; and releasing pressurized gas from within the open interior through the at least one vent.

2. The method of claim 1, wherein occluding the at least one vent comprises:

translating an elastomeric seal within the fill port between a first position that opens the at least one vent to fluid communication with the open interior and a second position that occludes the at least one vent from fluid communication with the open interior.

3. The method of claim 1, wherein releasing pressurized gas from within the open interior exhausts anesthetic agent through the at least one vent.

4. The method of claim 3, further comprising directing the exhausted anesthetic agent through the at least one vent in a pre-determined direction.

5. The method of claim 4, wherein the at least one vent directs anesthetic agent to a gas scavenger.

6. The method of claim 4, wherein the at least one vent directs anesthetic agent to an expansion chamber.

7. The method of claim 6, wherein the at least one vent directs anesthetic agent to a retainer disposed within the expansion chamber.

8. The method of claim 1, wherein opening the at least one vent comprises:

translating an elastomeric seal within the fill port from a second position that occludes the at least one vent from fluid communication with the open interior and a first position that opens the at least one vent to fluid communication with the open interior.

9. The method of claim 1, wherein opening fluid communication between the open interior and an agent reservoir comprises:

actuating a valve disposed between the open interior and the agent reservoir.

* * * * *